(12) United States Patent
Blanc

(10) Patent No.: US 10,288,594 B2
(45) Date of Patent: May 14, 2019

(54) METHOD AND DEVICE FOR OPTICALLY ANALYSING FRUIT OR VEGETABLES AND DEVICE FOR AUTOMATIC SORTING

(71) Applicant: MAF AGROBOTIC, Montauban (FR)

(72) Inventor: Philippe Blanc, Montauban (FR)

(73) Assignee: MAF AGROBOTIC, Montauban (FR)

( * ) Notice: Subject to any disclaimer, the term of this patent is extended or adjusted under 35 U.S.C. 154(b) by 0 days.

(21) Appl. No.: 15/909,130

(22) Filed: Mar. 1, 2018

(65) Prior Publication Data

US 2018/0252691 A1  Sep. 6, 2018

(30) Foreign Application Priority Data

Mar. 1, 2017 (FR) ...................... 17 51683

(51) Int. Cl.
| | |
|---|---|
| *G01C 3/08* | (2006.01) |
| *G01N 33/02* | (2006.01) |
| *G01N 21/3563* | (2014.01) |
| *B07C 5/342* | (2006.01) |
| *G01N 21/85* | (2006.01) |

(52) U.S. Cl.
CPC .......... *G01N 33/025* (2013.01); *B07C 5/342* (2013.01); *G01N 21/3563* (2013.01); *G01N 21/85* (2013.01); *B07C 2501/009* (2013.01)

(58) Field of Classification Search
CPC .. G01N 33/025; G01N 21/3563; G01N 21/85; B07C 5/342; B07C 2501/009
See application file for complete search history.

(56) References Cited

U.S. PATENT DOCUMENTS

| | | | |
|---|---|---|---|
| 5,626,238 A | 5/1997 | Blanc | |
| 6,888,082 B1 | 5/2005 | Blanc | |
| 2002/0008055 A1 | 1/2002 | Campbell et al. | |
| 2006/0037892 A1 | 2/2006 | Blanc | |
| 2013/0325346 A1* | 12/2013 | McPeek | G01N 33/0098 702/2 |
| 2017/0155852 A1* | 6/2017 | von Cramon | H04N 5/332 |
| 2018/0071788 A1* | 3/2018 | Anup | B07C 5/342 |

FOREIGN PATENT DOCUMENTS

| | | |
|---|---|---|
| FR | 2874424 A1 | 2/2006 |
| FR | 2985025 A1 | 6/2013 |
| GB | 2498086 B | 11/2015 |
| WO | 0101071 A1 | 1/2001 |
| WO | 2016054408 A2 | 4/2016 |

OTHER PUBLICATIONS

French Search Report, dated Nov. 23, 2017, from corresponding French application No. FR 1751683.
Sun, Jason, et al. "Multispectral scattering imaging and NIR interactance for apple firmness predictions." Postharvest Biology and Technology 119 (2016): 58-68.

* cited by examiner

*Primary Examiner* — Samantha K Abraham
(74) *Attorney, Agent, or Firm* — Ipsilon USA, LLP

(57) ABSTRACT

Disclosed is a method and a device for optically analyzing fruit or vegetables. Different light sources are adapted to apply light radiation in different wavelength ranges selectively to each object according to a predetermined illumination sequence, and images are produced by at least one color camera sensitive to infrared, the exposure of which is controlled in synchronism with the illumination sequence so as to produce a plurality of images in different wavelength ranges, including at least one image in a visible range and at least one image in an infrared range.

20 Claims, 6 Drawing Sheets

ETAT DE LA TECHNIQUE

ETAT DE LA TECHNIQUE

Figure 1:
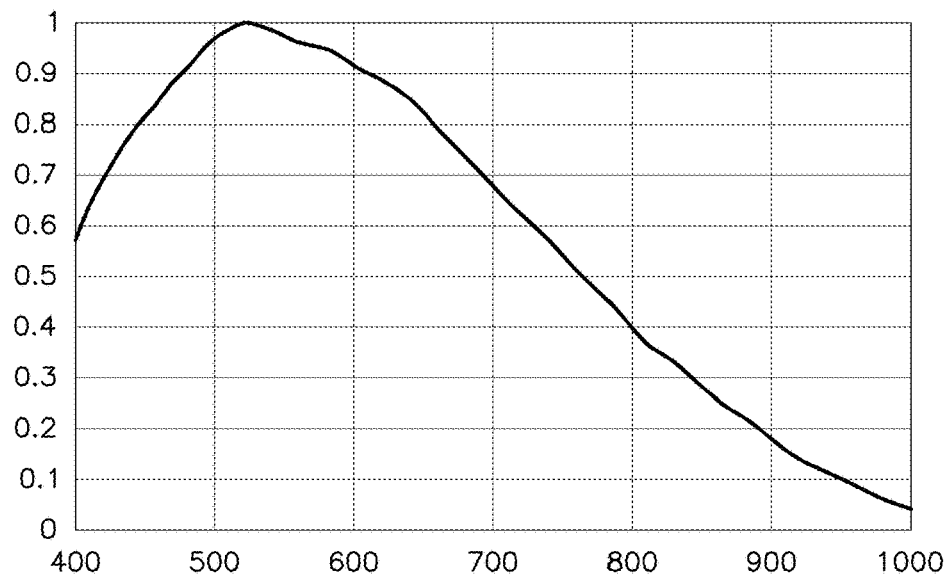

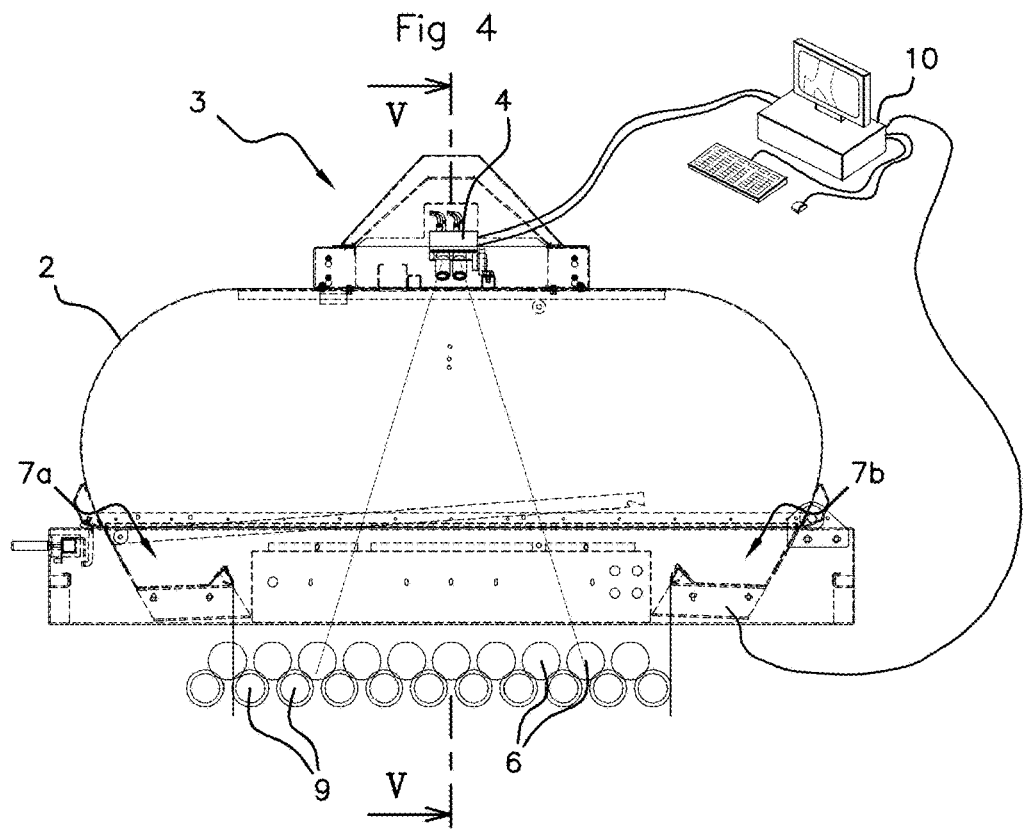
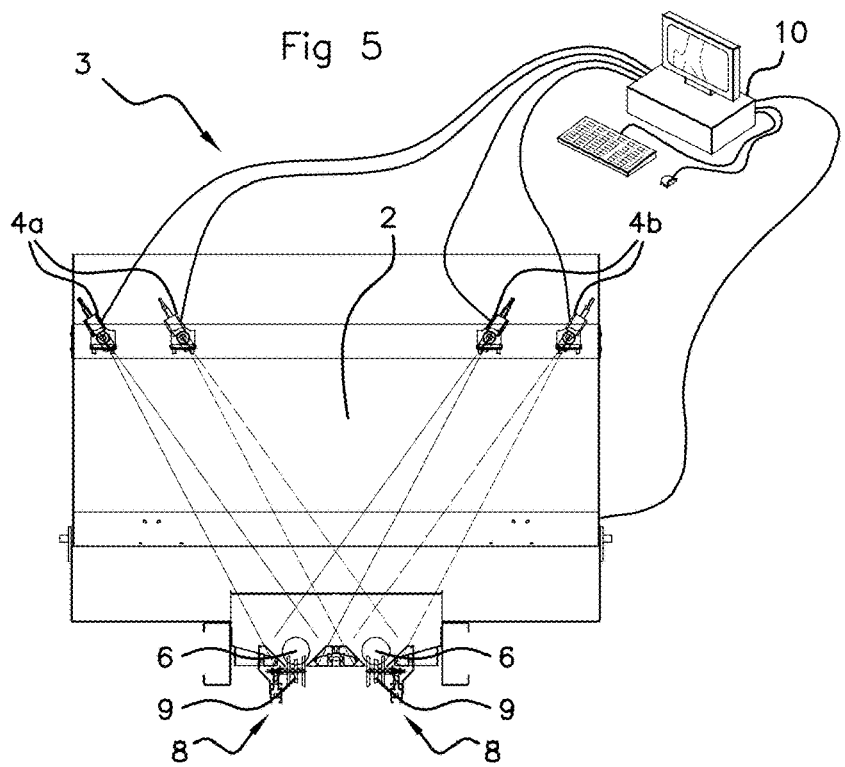

METHOD AND DEVICE FOR OPTICALLY ANALYSING FRUIT OR VEGETABLES AND DEVICE FOR AUTOMATIC SORTING

The invention relates to a method and a device for optically analysing fruit or vegetables for the purpose of automatically sorting them. It relates to a device for automatically sorting fruit or vegetables using a method of optical analysis in accordance with the invention and/or comprising an optical analysis device in accordance with the invention.

It is known that the optical analysis of fruit or vegetables by imaging in a wavelength band typically between 250 nm and 1000 nm, i.e. ultraviolet to infrared passing through the visible range, permits contactless measurement of different parameters, in particular dimensions (size), sugar level, acidity, maturity, firmness, presence of external or internal defects, colour . . . . However, in order to do so it is necessary to multiply the illumination devices and/or imaging devices in order to activate, for each parameter to be measured, an optical analysis in a wavelength range suitable for measuring this parameter. Furthermore, the measurement of a single parameter can necessitate a number of illumination wavelength ranges and/or a number of imaging wavelength ranges, even a number of different images for a single illumination and/or imaging wavelength range, e.g. a reflection image and a transmission image.

The publication Sun Jason et al «Multispectral scattering imaging and NIR interactance for apple firmness predictions» Potharvest Biology and Technology, vol. 119, 2016, pages 58-68 describes a multispectral imaging technique using reflectance spectroscopy measurements at a spatial resolution permitting evaluation of the firmness of apples. This technique consists of applying laser beams to the apple at different wavelengths, focussed by a 50 µm aperture and of capturing the image backscattered by the apple. Apart from the fact that it is limited to the prediction of firmness, this technique does not permit analysis of all the possible defects over the entire surface of the apple.

It should be noted that the imaging optical analysis techniques are distinguished in particular from spectrometric or spectroscopic techniques which permit only analysis of the light from a focussed source such as an optical fibre or laser, and thus of a very localised point of each object.

Moreover, the optical analysis of the objects must be carried out on the different portions of the external surface of the objects which are generally rotated while being transported in front of the illumination devices and cameras (cf. e.g. WO 01/01071, FR 2874424). It is not uncommon for an optical analysis in even a single illumination and/or imaging wavelength range to necessitate a multiplicity of illumination devices and/or cameras.

In order to carry out an imaging optical analysis in a number of wavelength ranges, it is thus necessary to multiply the illumination devices and/or the cameras and/or the filters placed before the illumination devices or before the cameras in order to select the different wavelength ranges. At least one monochrome camera is used for imaging in the ultraviolet and infrared ranges. For imaging in the visible range at least one colour camera is generally used, i.e. a trichromic camera comprising at least one CMOS or CCD sensor or the like.

Thus, in practice, each optical analysis station of an automatic sorting device for fruit or vegetables has thus far comprised a plurality of cameras, at least one camera per imaging wavelength range, i.e. classically between four and eight cameras per line for imaging each portion of the external surface of each object.

These different devices are particularly expensive, delicate, large and bulky and require regular and expensive maintenance. In this regard it should be noted in particular that they are subjected to relatively harsh environmental conditions (humid and dirty), as found in the processing and sorting of fruit or vegetables.

Furthermore, the use of filters to select the wavelengths is particularly expensive, such filters being difficult to purchase and degrading rapidly over time.

In addition, the transmission to an automated machine, formed of a computer system, of the different images supplied by the different cameras and the processing thereof by this computer system, in particular for the purpose of automatically sorting the objects, necessitate a period of time which, although brief as an absolute value, is not inconsiderable in the context of the most modern automatic sorting devices which can operate at a very high rate, typically at more than ten—in particular up to about fifty or even more—fruits or vegetables per second and per conveying line. Thus this transmission and processing time in the known optical analysis methods and devices is likely to constitute a restraint on increasing the rates of certain automatic sorting devices for fruit or vegetables.

The invention thus aims to overcome these disadvantages.

It aims in particular to propose a method and device for optically analysing fruit or vegetables by imaging in a plurality of wavelength ranges, which are considerably simplified and less expensive to install, use and maintain.

It aims in particular to propose such a method and such a device for optical analysis which can be without filters for the selection of imaging wavelength ranges.

It aims in particular to propose such a method and device for optical analysis which are more compatible with the environmental conditions of the automatic sorting of fruit or vegetables, and permit different parameters to be measured at a very high rate and at lower cost. It aims in particular to propose an optical analysis of fruit or vegetables by imaging, which is compatible with automatic sorting at a very high rate, i.e. which does not itself constitute a limit on increasing the automatic sorting rate.

It also aims to permit optical analysis of all the sorting criteria, other than weight, of the fruit or vegetables exclusively by imaging in different wavelength ranges.

It also aims to propose a device for automatically sorting objects such as fruit or vegetables, which have the same advantages.

Throughout the text the following terminology will be adopted:
"light radiation" designates any electromagnetic radiation of a wavelength between 200 nm and 1000 nm;
"wavelength range" designates any wavelength or wavelength band;
"visible range" designates any wavelength range included in the wavelength band between 380 nm and 700 nm;
"infrared range" designates any wavelength range included in the wavelength band between 700 nm and 1000 nm;
"ultraviolet range" designates any wavelength range included in the wavelength band between 200 nm and 380 nm.

The invention thus relates to a method of optically analysing objects belonging to the fruit and vegetable group in which images representative of the objects are produced in different imaging wavelength ranges, characterised in that:

a plurality of light sources formed of light-emitting diodes are arranged to be able each to apply light radiation to at least an external surface portion of at least one object, named illuminated object, the different light sources being adapted to be able to apply light radiation in different illumination wavelength ranges selectively to each illuminated object, the light radiation from at least one light source is applied to the whole of a face which is visible (by this light radiation) of the external surface of each object illuminated by this light source, the light sources are controlled according to a predetermined illumination sequence for each illuminated object in succession according to said different illumination wavelength ranges, images are produced by at least one—in particular one and only one—colour camera sensitive to light radiation in the visible range and to light radiation in the infrared range, named multispectral camera, orientated towards an external surface portion of at least one illuminated object corresponding to the whole visible face of the external surface of the object on the optical axis of the multispectral camera, and of which the exposure is controlled in synchronism with said illumination sequence so as to produce, with this same multispectral camera, a plurality of images in different imaging wavelength ranges of said external surface portion of at least one illuminated object, including at least one image in a visible range and at least one image in an infrared range, each multispectral camera is chosen from the group of cameras comprising a CMOS sensor with a matrix of colour filters without an infrared cut-off filter; and cameras comprising three CMOS sensors, one CMOS sensor for each primary colour, without an infrared cut-off filter.

The invention also relates to a device for optically analysing objects belonging to the fruit and vegetable group comprising means for producing images of the objects in different wavelength ranges, characterised in that it comprises:

an illumination device comprising a plurality of light sources formed of light-emitting diodes arranged to be able each to apply light radiation to at least an external surface portion of at least one object, named illuminated object, the different light sources being adapted to be able to apply light radiation in different illumination wavelength ranges selectively to each illuminated object, the illumination device being adapted to be able to apply light radiation from at least one light source to the whole of a visible face of the external surface of each object illuminated by this light source, a control device adapted to be able to control these light sources according to a predetermined illumination sequence for each illuminated object in succession according to said different illumination wavelength ranges, at least one—in particular one and only one—colour camera sensitive to light radiation in the visible range and to light radiation in the infrared range, named multispectral camera, orientated towards an external surface portion of at least one illuminated object corresponding to the whole visible face of the external surface of the object on the optical axis of the multispectral camera, each multispectral camera being chosen in the group of cameras comprising a CMOS sensor with a matrix of colour filters without an infrared cut-off filter; and cameras comprising three CMOS sensors, a CMOS sensor for each primary colour, without an infrared cut-off filter, and in that said control device is adapted to control the exposure of each multispectral camera in synchronism with said illumination sequence so as to produce with this same multispectral camera a plurality of images in different imaging wavelength ranges of said external surface portion of at least one illuminated object, including at least one image in a visible range and at least one image in an infrared range.

The invention also relates to a device for automatically sorting objects belonging to the fruit and vegetable group according to predetermined sorting criteria comprising:

at least one conveying line able to transport the objects in front of stations for analysing the objects in accordance with said sorting criteria, including at least one optical analysis station, an automated machine connected to the analysis stations to receive analysis signals therefrom, stations for discharging the objects in a plurality of discharging regions, the automated machine being programmed to control the selective discharging of each object into a discharging region selected in accordance with the analysis signals received by this automated machine for this object, characterised in that it comprises at least one optical analysis station formed by an optical analysis device in accordance with the invention.

The inventor has actually unexpectedly discovered that it is possible to use a single colour camera sensitive to light radiation in the visible range and to light radiation in the infrared range to produce a plurality of images in different imaging wavelength ranges, including at least one image in a visible range and at least one image in an infrared range. It will in fact suffice on the one hand to choose a colour camera which is sensitive to infrared (and in particular without an infrared cut-off filter), and, if necessary, to adjust the settings of this colour camera in order to produce each image in an infrared range according to the sensitivity of each colour of the camera in the infrared range in question.

By virtue of the invention, all the images necessary for the optical analysis of the objects in the visible and infrared ranges can be produced with a single multispectral camera controlled in synchronism with a suitable illumination sequence. This results in a considerable saving in equipment and a great simplification of each optical analysis station.

In some advantageous embodiments of a method in accordance with the invention, at least one multispectral camera is used which is fitted with a buffer memory for recording the different images which can be taken by this camera. Thus, said plurality of images of said external surface portion produced by a single multispectral camera is recorded in a buffer memory of this multispectral camera. Similarly, in an advantageous manner, in an optical analysis device in accordance with the invention, each multispectral camera is fitted with a buffer memory for storing images. Thus the different images produced during each illumination sequence can be produced at very high speed, at the maximum speed of image acquisition by each multispectral camera, and stored in a buffer memory of each multispectral camera before they are transmitted to an automated machine (computer system) for processing these images, which can carry out image processing at a much slower speed. Consequently, in particular, the bandwidth of the connection between each multispectral camera (which is typically a USB3 connection) and the automated machine no longer constitutes a limit on the increase in the rates of automatic sorting of the fruit or vegetables.

Each multispectral camera is a colour camera, i.e. a trichromic camera having sensors respectively sensitive to one of the three primary colours, red, green and blue. Any colour camera which is also sensitive to infrared, i.e. in particular without an infrared cut-off filter, can be used as a multispectral camera in a device and method for optical analysis in accordance with the invention. In particular, each multispectral camera can be chosen in the group of cameras comprising a CMOS sensor (with a matrix of colour filters such as a Bayer matrix); and cameras comprising three CMOS sensors (one CMOS sensor for each primary colour). However, there is nothing to prevent the use of a camera with a CCD sensor or sensors or the like.

Each multispectral camera is preferably a colour camera comprising a CMOS sensor and a matrix of colour filters, without an infrared cut-off filter. In fact, it proves to be the case that such a camera is effectively sensitive to infrared and can be adapted to produce images in any visible range and in any infrared range.

A colour camera of the type with a CMOS sensor or sensors comprises three groups of photosensitive elements, each group detecting one of the primary colours. In certain preferred embodiments, in a method in accordance with the invention, each image in an infrared range is produced with an adjustment of the white balance according to the sensitivity for each colour (i.e. of each group of elements which are photosensitive to one of the primary colours) of the multispectral camera in said infrared range. Furthermore, in these embodiments, a device in accordance with the invention for the production of each image in an infrared range, said control device is adapted to adjust the white balance according to the sensitivity of each colour of the multispectral camera in said infrared range. Thus a higher quality infrared image is obtained.

In fact, it has been discovered that the sensitivity of each group of photosensitive elements of a colour camera for an infrared wavelength varies according to the detection colour of this group of photosensitive elements. If said infrared range comprises a single infrared wavelength, the white balance is adjusted according to the sensitivity of each colour of the multispectral camera for this infrared wavelength. If said infrared range comprises an infrared wavelength band, the white balance can be adjusted according to the sensitivity of each colour of the multispectral camera for a characteristic wavelength, in particular the central wavelength, of said infrared wavelength band.

However, it should be noted that there is nothing to prevent the provision, as a variation, of the production of infrared images without adjustment of the white balance.

Various imaging techniques can be used in a method and a device for optical analysis in accordance with the invention, and different imaging techniques can be combined with a single multispectral camera and/or with different multispectral cameras. In particular, in a method and a device for optical analysis in accordance with the invention, said images produced by a single multispectral camera can equally be images produced by reflection and/or images produced by transmission and/or images produced by diffusion.

Similarly, each illumination wavelength range may or may not correspond to each imaging wavelength range. Thus, for example, it is possible to illuminate the object in a visible range and to produce images with a multispectral camera in this same visible range; to illuminate the object in an infrared range and to produce images with a multispectral camera in this same infrared range; to illuminate the object in an ultraviolet range and to produce images with a multispectral camera in a visible range (by fluorescence); etc.

For the production of reflection images the external surface region of the object illuminated by at least one light source is the whole of a face of the external surface of the object visible by the light radiation of this light source, and at least one multispectral camera is arranged with respect to this light source to produce reflection images of the whole of this visible face. Thus, in order to produce a reflection image, at least one light source applies light radiation to said external surface portion of the illuminated object towards which the multispectral camera is orientated.

In order to produce a transmission image, at least one light source applies light radiation to an external surface region of the object diametrically opposite to said external surface portion of the illuminated object towards which the multispectral camera is orientated. In order to produce a diffusion image at least one light source applies light radiation to a region, named illuminated region, of the external surface of the object separate from said external surface portion of the illuminated object towards which the multispectral camera is orientated, the multispectral camera being orientated with respect to this illuminated region at an imaging angle greater than 90° and less than 180°.

This being the case, in some advantageous embodiments in accordance with the invention, at least one multispectral camera is arranged with respect to said light sources in order to produce only reflection images. In fact, in numerous applications, the optical analysis of fruit or vegetables can be carried out exclusively with such reflection images. Such is the case in particular for the optical analysis of fruits from the group comprising apples, pears, stone fruits (peaches, nectarines, apricots . . . ) and tomatoes.

In other embodiments in accordance with the invention, at least one multispectral camera can be arranged with respect to at least some of the light sources in order to produce diffusion/transmission images, in particular in a visible range. Such is the case in particular for the optical analysis of citrus fruits. In an advantageous manner, at least others of the light sources can be arranged with respect to the multispectral camera in order to permit the production of reflection images, in particular reflection images in an infrared range under illumination in an infrared range and/or reflection images in a visible range under illumination in a visible range and/or reflection images in the visible range under illumination in an ultraviolet range.

Advantageously and in accordance with the invention at least one light source is arranged to be able to apply light radiation to the whole of the visible face of the external surface of each object illuminated by this light source.

In fact, according to the imaging technique concerned, the external surface region of the object illuminated by each light source can equally be:
  the whole of a visible face of the external surface of the object in the direction of propagation of said light radiation emitted by this light source and applied to the external surface of the object—in particular a diametral segment of the object when this object is generally spherical; this is advantageously the case in particular for the production of reflection images;
  a region where said light radiation is focussed on the external surface of the object, this focussing region being smaller than the visible face of the external surface of the object in the direction of propagation of said light radiation—in particular smaller than a diametral segment of the object when this object is generally spherical; this is advantageously the case in particular for the production of diffusion/transmission images.

Moreover, there is nothing to prevent certain images produced by a multispectral camera in accordance with the invention from not representing the whole of the visible face of the external surface of the object on the optical axis of the camera. Thus said external surface portion of the illuminated object can, in some embodiments and for at least one multispectral camera, correspond to an external surface portion of the object which is smaller than a visible face of this external surface on the optical axis of the camera.

This being the case, in certain preferred embodiments, at least one multispectral camera is arranged with respect to the illuminated object so that said external surface portion of the illuminated object, of which images are produced by the multispectral camera, corresponds to the whole visible face of the external surface of the object on the optical axis of the multispectral camera. Thus, when the object is generally spherical, the images produced by the multispectral camera are images of a diametral segment of the object.

Moreover, said illumination sequence and the synchronisation of the exposure of each multispectral camera with respect to this illumination sequence can be the object of numerous embodiment variations.

In particular, in some advantageous embodiments according to the invention, said illumination sequence is formed of a succession of illumination periods, some of said light sources being activated during each illumination period, this group of said light sources being chosen to illuminate each object in one of said illumination wavelength ranges. Furthermore, the illumination wavelength ranges of two successive illumination periods are preferably distinct from one another.

Each illumination period can be particularly brief, the exposure period of the multispectral camera within an illumination period also being able to be particularly brief, the image produced during this exposure period being able to be recorded in a buffer memory of the multispectral camera. Thus, in certain advantageous embodiments in accordance with the invention, each illumination period of said illumination sequence is between 0.1 ms and 5 ms—in particular between 0.1 ms and 1.5 ms.

Similarly, there is nothing to prevent the different successive illumination periods of an illumination sequence being separated from one another by periods when all of said light sources are switched off. These switched-off periods are advantageously between e.g. 0.05 ms and 0.5 ms, in particular of the order of 0.1 ms. Nevertheless, the different illumination periods of a single illumination sequence preferably succeed one another without interruption, i.e. with no switched-off period between two illumination periods.

The exposure of a multispectral camera is preferably triggered with a delay with respect to the activation of an illumination period, this delay being chosen so that each light source of said group of said light sources of this illumination period is effectively completely switched on and active before the multispectral camera is triggered. In fact, the light sources, including the ultrafast control LEDs, necessitate a certain delay between receiving their activation signal and being fully switched on. This delay is between e.g. 0.01 ms and 0.5 ms, in particular of the order of 0.05 ms.

Similarly, shutting off the exposure of the multispectral camera is preferably triggered in advance with respect to the switching-off of at least one of the light sources. Thus, it is ensured that for each illumination period, each corresponding light source is, and remains, completely active and switched on throughout the exposure period of the multispectral camera. This advance is between e.g. 0.01 ms and 0.5 ms, in particular of the order of 0.05 ms.

Thus, it is possible e.g. to use a single multispectral camera to produce series of images comprising between two and ten—in particular from three to five—successive images of a single illuminated object in different wavelength ranges, including at least one image in a visible range and at least one image in an infrared range, during one illumination sequence over a total time period for the illumination sequence of less than 10 ms, in particular between 1 ms and 5 ms. For example, it is possible to produce a series of four successive images over a total period of the order of 3.5 ms. The number and nature of each image of a single series of images in different wavelength ranges are chosen so as to permit the optical analysis of the fruit or vegetables to be sorted from these different images. They can form the object of very many variations according to the important sorting criteria for these fruit or vegetables, which can vary from one variety of fruit or vegetables to another and/or depending upon the end client's requirements with respect to the sorting of fruit or vegetables.

Furthermore, the different light sources are chosen so as to be compatible with said illumination sequence and with the different illumination wavelength ranges and with the characteristics of each multispectral camera used. In particular, in certain advantageous embodiments, said light sources comprise at least one ultrafast control LED. In particular, said light sources comprise at least one visible white light illumination LED, at least one ultraviolet light radiation illumination LED—in particular an ultraviolet illumination LED with a wavelength between 250 nm and 380 nm, e.g. 365 nm—and at least one infrared illumination LED—in particular an infrared illumination LED with a wavelength between 720 and 780 nm, e.g. 740 nm; an infrared illumination LED with a wavelength between 800 nm and 850 nm, e.g. 810 nm; and an infrared illumination LED with a wavelength between 900 nm and 1000 nm, e.g. 940 nm. Other examples are possible.

In some advantageous embodiments in accordance with the invention, said light sources are mounted in an optical chamber having a reflective internal surface of a shape which is chosen depending on the position of the light sources so as to permit uniform illumination of the objects in the optical field of said at least one multispectral camera. Such uniform illumination is homogeneous illumination of the whole face of each object exposed to the light radiation from the optical chamber. Furthermore, at least one multispectral camera is orientated so as to produce reflection images of the whole face of each object thus illuminated.

A method and a device for optical analysis in accordance with the invention make it possible in particular to optically analyse fruit or vegetables even as they are being moved by a conveyor—in particular a high-speed conveyor, e.g. a conveyor permitting transportation of more than ten objects per second, in particular up to fifty objects per second or even more, in front of each multispectral camera. Thus, in some embodiments of a method in accordance with the invention, each illuminated object is moved by a conveyor during said illumination sequence.

Similarly, a method and device for optical analysis in accordance with the invention make it possible to optically analyse fruit or vegetables while they are being rotated on themselves. Thus, in some embodiments of a method in accordance with the invention, each illuminated object is rotated on itself during said illumination sequence.

The invention makes possible a considerable reduction in the complexity, number and size of each optical analysis station of a device for automatically sorting fruit or vegetables. In particular, in certain embodiments of a device for automatically sorting fruit or vegetables in accordance with the invention, each optical analysis station comprises less than four multispectral cameras—in particular one multispectral camera or two multispectral cameras—per conveying line. In fact, it proves to be the case that it is possible to use a single multispectral camera to produce all of the images of a single external surface portion of the objects which are necessary for the optical analysis of the fruit or vegetables for the purpose of automatically sorting them: size, colour, internal defects, external defects and firmness. For example, when the objects as a whole are rotationally symmetrical—in particular generally spherical, which is the case for most fruit or vegetables, each optical analysis station can comprise, for each conveying line, only one multispectral camera (or two multispectral camera laterally offset and inclined with respect to the vertical, one on each side of the line) in order to produce images of the whole external surface of the objects during their passage through the optical analysis station, each object being rotated by at least 180° on itself between entering the field of the multispectral camera and leaving the field of the multispectral camera.

In some embodiments of the invention it is even possible to make provision for the automatic sorting device to comprise a single optical analysis station. This is particularly the case for the automatic sorting of fruit or vegetables chosen from the group consisting of apples, pears, kiwi fruit, citrus fruit, tomatoes, peaches, apricots, nectarines, plums, persimmons, avocados, mangoes, pomegranates, cantaloupe melons, blueberries, cherries. Other examples are possible.

The invention likewise relates to a method and a device for optically analysing fruit or vegetables, and a device for automatically sorting fruit or vegetables, characterised in combination by all or some of the features mentioned above or below.

Figure 2:
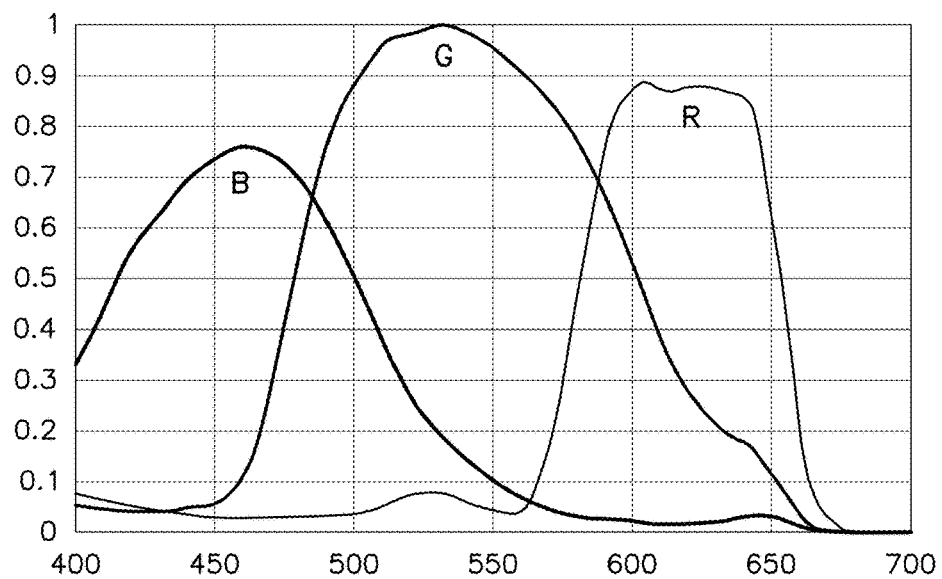
Figure 3:
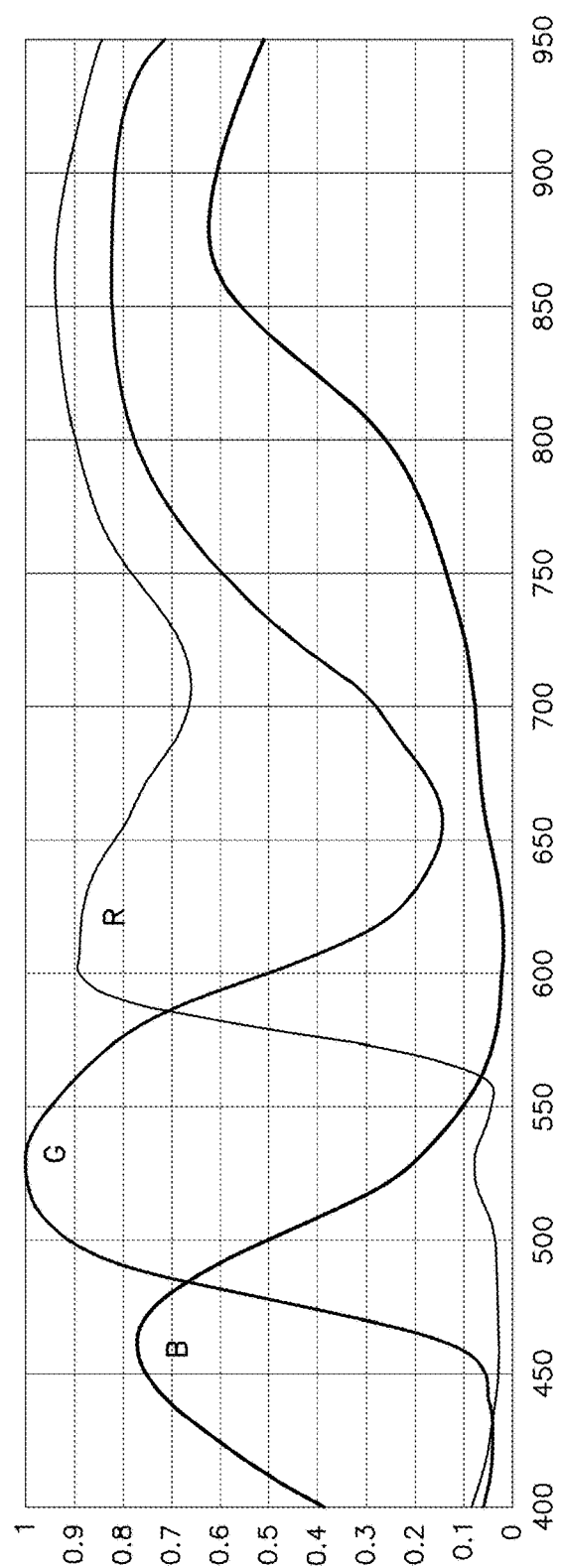
Figure 6:
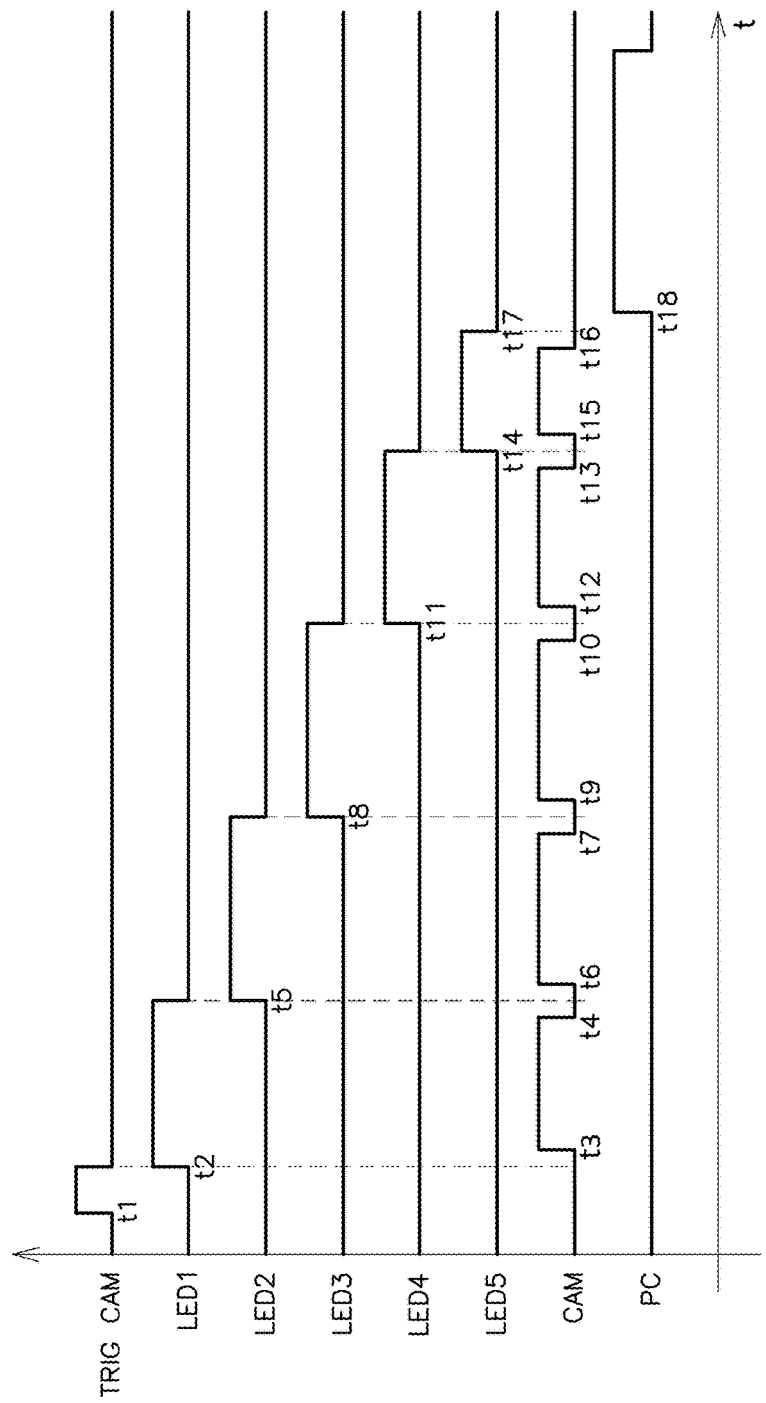
Figure 7:
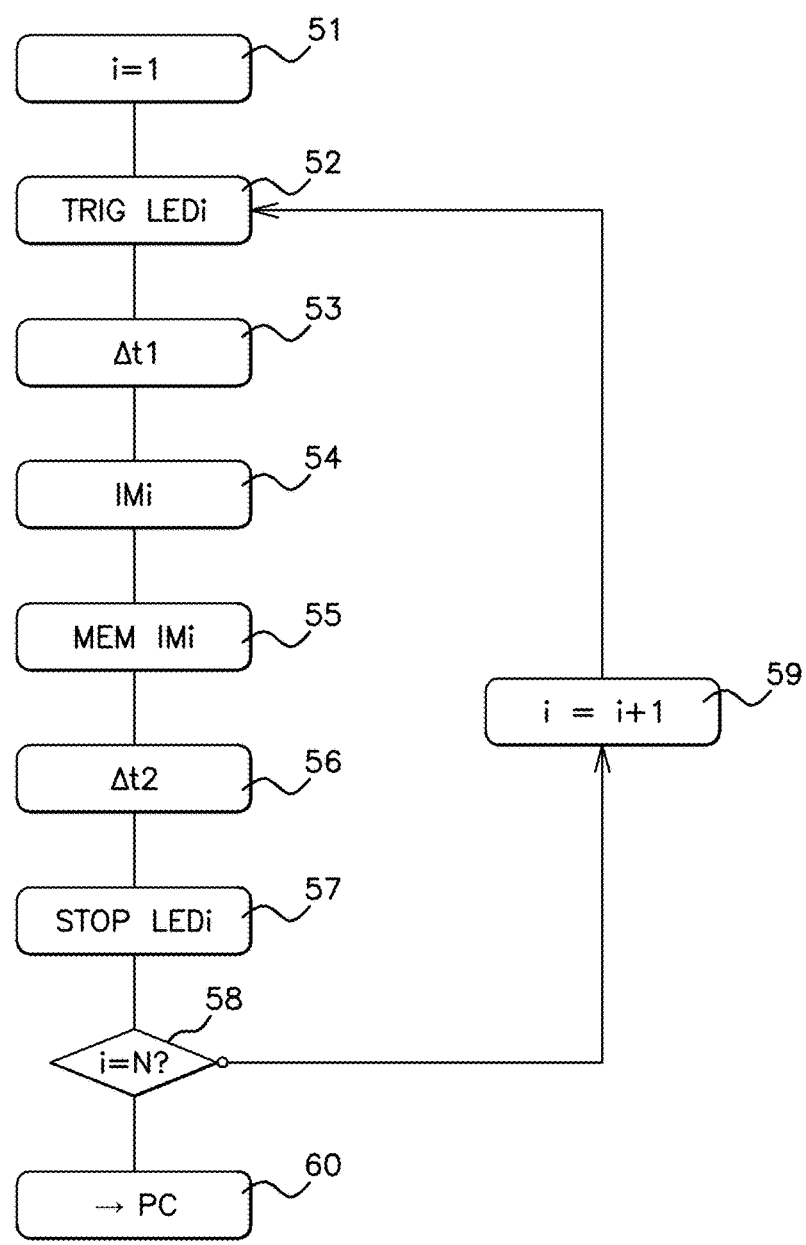
Figure 8:
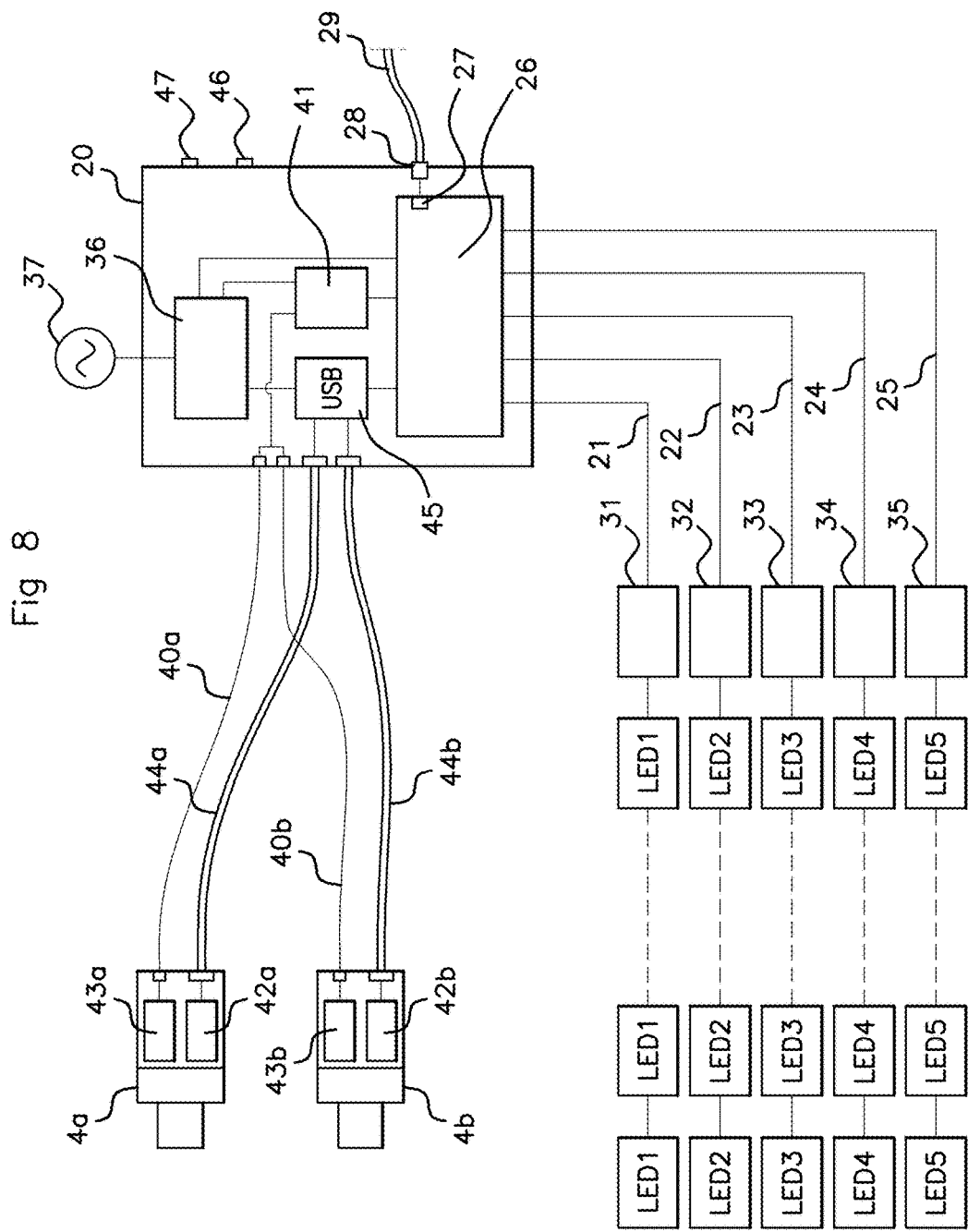

Other aims, features and advantages of the invention will become apparent upon reading the following description of some of its embodiments given by way of non-limiting example and with reference to the attached figures in which:

FIG. 1 is an example of a spectrum of sensitivity of a monochrome camera used in a prior art optical analysis device, FIG. 2 is an example of a spectrum of sensitivity of a colour camera used in a prior art optical analysis device, FIG. 3 is an example of a spectrum of sensitivity of a colour camera sensitive to infrared and which can be used as a multispectral camera in a method an device for optical analysis in accordance with the invention, FIG. 4 is a schematic elevation view of an optical analysis station of an automatic sorting device in accordance with one embodiment of the invention, FIG. 5 is a schematic, transverse cross-sectional view along line V-V in FIG. 4, FIG. 6 is a timing diagram of an example of an illumination and imaging sequence of an optical analysis method in accordance with the invention, FIG. 7 is an operating diagram of steps during an illumination sequence of an embodiment of an optical analysis method in accordance with the invention, FIG. 8 is an operating diagram of the cameras, light sources and a device for controlling the cameras and light sources of an optical analysis device in accordance with the invention for a line for conveying objects.

FIG. 1 is a spectrum of sensitivity of a monochrome camera comprising a CMOS sensor conventionally used in the prior art for optical analysis for the purpose of automatically sorting fruit or vegetables by infrared and/or ultraviolet imaging. As shown, the sensitivity of the camera in the infrared range is not zero but is relatively low. The same is true in the ultraviolet range. FIG. 2 is a spectrum of sensitivity of a colour camera comprising a CMOS sensor and a Bayer filter matrix, as well as an infrared cut-off filter, conventionally used in the prior art for optical analysis for the purpose of automatically sorting fruit or vegetables by imaging in the visible range. As shown, such a colour camera is totally insensitive in the infrared range.

In contrast, the inventor has unexpectedly discovered that a colour camera without an infrared cut-off filter is actually particularly sensitive in the infrared range, as shown in FIG. 3, and can thus be used equally well in the visible range and in the infrared range, making it possible to simplify considerably the optical analysis stations in the devices for automatically sorting fruit or vegetables. The invention thus consists of using a single colour camera to produce images in at least one visible range and images in at least one infrared range, and possibly images in at least one ultraviolet range, at the same time.

One exemplified embodiment of an optical analysis device 3 in accordance with the invention is illustrated in FIGS. 4 and 5. This optical analysis device constitutes an optical analysis station of an automatic sorting device with general characteristics which are well known in themselves (cf. e.g. U.S. Pat. No. 5,626,238) and which can form the object of very many embodiment variations, the invention being applicable to all these embodiment variations, without limitation, since the automatic sorting device makes it possible to move a plurality of objects 6 formed by fruit or vegetables in horizontal translation one after another in front of the optical analysis device on supports 9 arranged on at least one conveying line 8, generally on a plurality of parallel conveying lines 8 for fruit or vegetables as in the illustrated example.

The supports 9 are preferably rotating supports such as rollers which are driven not only in longitudinal translation but also in rotation on themselves about transverse axes of rotation making it possible to rotate the objects 6 on themselves as they are passing through the optical analysis device. In fact, generally speaking, fruit or vegetables have at least one degree of rotational symmetry and can thus be rotated on themselves to permit production of imaging of the whole of their external surface by the different images acquired in succession of a single object 6 as it moves along the conveying line. The rollers are formed e.g. of a plurality of parallel discs, two rollers in succession in the longitudinal direction of translational movement defining a reception housing for an object 6.

The optical analysis device 3 in accordance with the invention comprises, in the illustrated example, two illumination devices 7a, 7b, of which one 7a is located upstream and one 7b is located downstream. The two illumination devices 7a, 7b are identical and each comprise a plurality of light sources formed of LEDs (light-emitting diodes) emitting light radiation in different illumination wavelength ranges.

For example, each illumination device 7a, 7b comprises at least one LED, named LED1, emitting white light in the visible range; at least one LED, named LED2, emitting light radiation in an infrared range at a wavelength between 720 and 780 nm, e.g. centred on 740 nm; at least one LED, named LED3, emitting light radiation in an infrared range at a wavelength between 800 nm and 850 nm, e.g. centred on 810 nm; at least one LED, named LED4, emitting light radiation in an infrared range at a wavelength between 900 nm and 1000 nm, e.g. centred on 940 nm; at least one LED, named LED5, emitting light radiation in an ultraviolet range at a wavelength between 250 nm and 380 nm, e.g. centred on 365 nm. Each illumination device 7a, 7b preferably comprises a plurality of LEDs switched on simultaneously for each illumination wavelength range.

The light sources LED1, LED2, LED3, LED4, LED5 are disposed above the conveying line 8 and orientated upwards so that they do not apply any direct illumination to the objects 6. The light sources LED1, LED2, LED3, LED4, LED5 are, on the other hand, mounted in an optical chamber 2, the internal surface of which is reflective. The optical chamber 2 also has an open base so that the radiation emitted by the light sources is reflected by the internal surface of the optical chamber and is directed towards the fruit or vegetables passing below the optical chamber 2.

The optical analysis device 3 in accordance with the invention comprises at least one colour camera 4 sensitive to infrared. It should be noted that, in a device in accordance with the invention, it is possible to provide just one camera 4.

In the illustrated example of an optical station for two parallel conveying lines 8, the optical analysis device 3 preferably comprises four cameras 4a, 4b disposed above the two conveying lines 8 for fruit or vegetables, in the upper part of the optical chamber 2, i.e. two cameras 4a, 4b for each conveying line 8.

The cameras 4a, 4b are arranged with their optical axis slightly inclined with respect to the vertical above the conveying lines 8. They are disposed respectively on one side and the other of the conveying line 8 which they produce images of, so that they acquire a substantially different image of each object 6, a first camera 4a making it possible to obtain an image of an upper portion and of a first lateral face of the object moved by the conveying line 8, and a second camera 4b making it possible to obtain an image of an upper portion and of a second lateral face (opposite to the first lateral face) of the object moved by the conveying line 8.

Each camera 4a, 4b has an optical field which covers a sufficient length of the corresponding conveying line 8 so that it can produce a plurality of images of each object 6 moved by this conveying line 8, including at least two images of two diametrically opposite portions of each object 6. Each image illustrates a plurality of successive objects 6 longitudinally along the conveying line 8, the processing of the images making it possible to identify each object in each image in a manner which is well known per se. Furthermore, the cameras each produce a plurality of series of successive images of a single object during its passing in front of the optical analysis device 3. In practice, it is possible to produce e.g. between 5 and 50 series of images of each object, typically of the order of 10 series of images of each object during transportation thereof in front of each camera, each image corresponding to a different portion of the external surface of the object, this object being rotated.

There is nothing to prevent other camera arrangements as a variation, e.g. with a single camera focussed longitudinally on a single object 6, the optical analysis device 3 then comprising a number of longitudinally successive cameras sufficient to permit production of the series of images of the whole external surface of each object and/or a single multispectral camera making it possible to produce images of objects moved by a plurality of parallel conveying lines 8, i.e. images in which objects are laterally juxtaposed.

As illustrated in FIG. 4, the shape of the internal surface of the optical chamber 2 is advantageously chosen depending on the position of the light sources of the illumination devices 7a, 7b so as to permit uniform illumination of the objects 6 located in the optical field of the cameras 4a, 4b of the optical analysis device 3.

Each camera 4a, 4b is a colour camera sensitive to infrared, e.g. chosen from the group of cameras comprising a CMOS sensor (with a matrix of colour filters such as a Bayer matrix but without an infrared cut-off filter); cameras comprising three CMOS sensors (one CMOS sensor for each primary colour) and without an infrared cut-off filter.

As illustrated, the cameras 4a, 4b are disposed above the conveying lines 8, with their optical axes orientated downwards and inclined towards one of the conveying lines 8.

Each camera 4a, 4b is fitted with an internal memory 42a, 42b respectively, making it possible to store a plurality of images successively produced by the camera. Thus, each camera can be controlled in burst mode in a high-speed sequence in order to produce successively a plurality of images of each object present in its optical field, the different images of a single series of images being able to be produced in different imaging wavelength ranges and stored in real time in the memory of the camera. Each camera 4a, 4b is preferably chosen so that its internal memory is sufficient to permit storage of a plurality of images successively produced by the camera during an illumination sequence, these different images corresponding to a series of images in different imaging wavelength ranges, this series of images permitting optical analysis of the different sorting criteria necessary to the automatic sorting of the objects. Furthermore, each camera 4a, 4b is preferably a high-definition camera, i.e. of more than 1 million pixels. For example, very good results have been obtained with cameras comprising a 1920×1200 pixel CMOS sensor.

For example, each series of images can comprise:
  an image produced by reflection while the object is illuminated by white light (by each LED1),
  an image produced by reflection while the object is illuminated in an infrared illumination range (by each LED2) at a wavelength between 720 and 780 nm, e.g. centred on 740 nm,
  an image produced by reflection while the object is illuminated in an infrared illumination range (by each LED3) at a wavelength between 800 nm and 850 nm, e.g. centred on 810 nm,
  an image produced by reflection while the object is illuminated in an infrared illumination range (by each LED4) at a wavelength between 900 nm and 1000 nm, e.g. centred on 940 nm,
  an image produced by reflection while the object is illuminated in an ultraviolet illumination range (by each LED5) at a wavelength between 250 nm and 380 nm, e.g. centred on 365 nm.

These different images make it possible in particular to detect and distinguish internal or external characteristics, diseases or defects, chosen from the group formed by scabs, bitter pit disease, various forms of rot, superficial sun scorching, parasites such as *Gloesporium*, sun-scalding, hail strikes, bruising, pitting, perforation and superficial roughness of the skin such as russeting.

Other examples are possible and in particular there is nothing to prevent making provision for also producing diffusion/transmission images, e.g. by focussing light radiation in the visible range on a region of the external surface of an object and producing an image with a camera of a portion of the external surface of the object separate from the focussing region, in particular with an optical axis of the camera forming an angle between 90° and 180° with respect to the axis of the light radiation. In order to do this it is not necessary to increase the number of cameras of the optical analysis device and it will suffice to provide e.g. a light source on the side and/or below each conveying line 8.

It should be noted that since each camera 4a, 4b is a colour camera sensitive to infrared and without filters other than those necessary to detect colours (in particular a Bayer filter matrix), each image produced covers the whole spectrum of sensitivity of the camera. Thus, when the objects are illuminated with white light, the image formed by the camera is a colour image in the visible imaging range. Similarly, when the objects are illuminated in an illumination wavelength range within the infrared, the image formed by the camera is an image produced in the same infrared wavelength range. And when the objects are illuminated by ultraviolet light radiation, the image formed by the camera is a colour representation of the fluorescence of the objects in the visible range.

Each light source LED1, LED2, LED3, LED4, LED5 and each camera 4a, 4b is controlled from a computer system 10 for analysis of the images acquired by the cameras 4a, 4b. This computer system 10 can be the object of any variations since it is adapted and programmed:
  to control the switching on and switching off of each light source in a predetermined illumination sequence to permit the production of each series of images,
  to receive the different images acquired by the different cameras,
  to analyse these images and deduce therefrom criteria for automatically sorting the objects,
  to control the automatic sorting device depending on the sorting criteria resulting from the optical analysis of the objects thus carried out.

Such a computer system 10 can comprise a single computing device such as a computer as illustrated in the figures, or a plurality of computing devices and/or computing resources and/or terminals and/or peripherals remote from one another and connected as a network. The computer system 10 can also be formed of a plurality of computing devices distinct from one another and not connected, each being dedicated to a specific function: e.g. a computing device to control the optical analysis device and thus to carry out the imaging and optical analysis of the objects; and another computing device for automatically sorting the objects. Moreover, the computer system 10 is adapted to be able to execute a computer program or a plurality of computer programs, in particular for implementation of a method in accordance with the invention.

The computer system 10 comprises an electronic board 20 to control (FIG. 8) the light sources LED1, LED2, LED3, LED4, LED5 and the cameras 4a, 4b. FIG. 8 shows only two cameras 4a, 4b orientated towards the same conveying line 8. Each light source LED1, LED2, LED3, LED4, LED5 is connected to the electronic control board 20 by a power-supply cable 21, 22, 23, 24, 25 appertaining respectively to each group of LEDs to be activated simultaneously, i.e. corresponding to a single illumination wavelength range, the switching on and switching off of the different light sources being controlled by this electronic control board 20. The different LEDs of each group of LEDs are preferably connected to the same (high-speed) control and power-supply board 31, 32, 33, 34, 35 respectively appertaining to this group of LEDs and receiving the power-supply cable 21, 22, 23, 24, 25.

The electronic control board 20 comprises an integrated circuit 26 which is e.g. a programmable integrated circuit (FPGA) to which the different power-supply cables 21, 22, 23, 24, 25 of the LED5 are directly connected. This integrated circuit 26 also has an input port 27 connected to a network connector 28 of the control board 20 onto which a cable 29 such as an Ethernet cable from a mother board of the computer system 10 can be plugged.

The electronic control board 20 also comprises an electric power-supply circuit 36 able to be connected to a source 37 of electrical energy, this electric power-supply circuit 36 supplying the different components of the electronic control board 20.

Each camera 4a, 4b is also connected to the electronic control board 20 by an electric cable 40a, 40b respectively, appertaining to each camera 4a, 4b so as to be able to be controlled thereby to be triggered in order to take an image or a series of images. Each electric cable 40a, 40b makes it possible to transmit to the camera a triggering signal TRIG CAM produced by a formatting circuit 41 upon command by the integrated circuit 26. Thus the integrated circuit 26 can trigger each camera 4a, 4b at a precisely defined moment by delivering a signal to the formatting circuit 41, this circuit formatting the triggering signal TRIG CAM and delivering it via the electric cables 40a, 40b.

Each camera 4a, 4b preferably comprises a programmable electronic sequencer circuit 43a, 43b respectively making it possible to program a predetermined imaging sequence corresponding to a series of images as defined above, i.e. corresponding itself to a predetermined illumination sequence. The triggering signal TRIG CAM thus makes it possible to trigger the sequencer of the camera and to initiate a previously programmed imaging sequence by each camera 4a, 4b. The sequencer 43a, 43b itself successively triggers each imaging operation by maintaining the exposure of the camera for a period corresponding to the capturing of an image. The sequencer 43a, 43b is also programmed to control the camera according to different photographic parameters adapted to the production of each image, in particular depending on the wavelength range in question.

In particular, in order to produce images in an infrared range the sequencer 43a, 43b adjusts the white balance of the camera so as to optimise the image quality depending on the sensitivity in the infrared range of each group of photosensitive elements to one of the primary colours of the camera. In fact, as seen in FIG. 3, the different groups of photosensitive elements in the different primary colours of the camera do not all have the same infrared sensitivity. It is thus advantageous to rebalance these sensitivity differences and to do so simply by adjusting the white balance of the camera before capturing the corresponding infrared image. This adjustment can be effected by previously experimentally measuring these differences in sensitivity for each infrared illumination wavelength, i.e. from the knowledge of the spectrum as illustrated in FIG. 3.

The computer system 10, its electronic control board 20 and each sequencer 43a, 43b of each multispectral camera together constitute a device for control of each illumination sequence and of each imaging sequence making it possible to produce each series of images by each multispectral camera.

Each camera 4a, 4b is also connected to the electronic control board 20 by a high-speed USB3 cable 44a, 44b respectively, on the one hand to be supplied with electric power, and on the other hand for the transmission of different images of a series of images to the computer system 10. These USB3 cables are connected to a USB3 multiport connection circuit 45 of the electronic control board 20.

The electronic control board 20 also advantageously comprises a button 46 enabling it to be switched on or off, an indicating light 47 enabling any possible malfunction to be indicated.

FIG. 6 illustrates an example of a timing diagram for an illumination sequence in accordance with the invention, making it possible to produce a series of images as mentioned above.

At the time t1, the electronic control board 20 emits the triggering signal TRIG CAM for the cameras 4$a$, 4$b$. Upon reception of this triggering signal, the sequencer of each camera executes the sequence for which it has been programmed and which corresponds to the signal CAM illustrated in FIG. 6. The first imaging operation is triggered at a time t3 after a short waiting period after the time t1 of reception of the triggering signal.

The electronic control board 20 also triggers the illumination sequence of the different light sources LED1, LED2, LED3, LED4, LED5 according to the corresponding signals illustrated in FIG. 6. As shown, the light sources LED1 are switched on at a time t2 immediately preceding the time t3 by a period sufficient to permit each corresponding LED to be switched on fully, following the activation of the corresponding control and power-supply board.

Each camera 4$a$, 4$b$ captures the image during a period dependant on the size of the image (number of pixels in a row and number of pixels in a column) and on the integration time of the camera. At the end of this period, at the time t4, a first image is captured by the camera and is stored in its memory 42$a$, 42$b$. It should be noted that throughout the period when the camera captures the image, the light sources LED1 remain fully switched on. At a time t5, subsequent to the time t4, the light sources LED 1 are switched off and the light sources LED2 corresponding to another illumination wavelength range are switched on. The time t5 is slightly offset from the time t4 of the end of image capture by the camera by a period which is as short as possible but sufficient to be able to ensure that the light sources remain switched on throughout this capture.

The cycle is repeated for the capture of four other images under illumination successively by the light sources LED2, then LED3, then LED4, then LED5. The capture of the second image commences at the time t6 and ends at the time t7. The light sources LED2 are switched off and the light sources LED3 are switched on at the subsequent time t8. The capture of the third image commences at the time t9 and ends at the time t10. The light sources LED3 are switched off and the light sources LED4 are switched on at the subsequent time t11. The capture of the fourth image commences at the time t12 and ends at the time t13. The light sources LED4 are switched off and the light sources LED5 are switched on at the subsequent time t14. The capture of the fifth image commences at the time t15 and ends at the time t16. The light sources LED5 are switched off at the subsequent time t17.

After capturing all of the images of a single series, all these images can then be transmitted, from the subsequent time t18 defined by the sequencer of each camera, to the computer system 10 via the USB3 cables 44$a$, 44$b$.

FIG. 7 illustrates a variation in which the electronic control board 20 triggers not only the switching on of the different light sources but also each camera if these cameras have no sequencer, for a sequence of illumination and capture of a series of images according to the timing diagram of FIG. 6.

In the first step 51 an index i representing each group LEDi of LEDs is initialised at 1. In the example mentioned above, i varies from 1 to N=5. In the subsequent step 52, the light sources LEDi are switched on. After a waiting period Δt1 (equal to t3−t2 for LED1) in step 53, the images IMi by the different cameras 4$a$, 4$b$ are captured (between t3 and t4 for LED1) in the subsequent step 54 then stored in the memory of each camera in step 55. After a waiting period Δt2 (equal to t5−t4 for LED1), in step 56, the light sources LEDi are switched off in the subsequent step 57, then a test 58 is carried out on the index i to determine whether or not the maximum value N of this index has been reached. If it has not been reached, the index i is incremented by 1 in step 59 and the process is repeated from step 52 to switch on the light sources of the following group. If it has been reached, the images are transmitted to the computer system 10 in step 60.

The invention thus makes possible an optical analysis of the objects using multispectral colour cameras sensitive to infrared in burst mode, making it possible to produce series of successive images at very high speed. Each series of images produced by a multispectral camera in accordance with the invention corresponds to one image produced by a prior art camera. However, instead of necessitating a plurality of cameras to produce these different images, the invention makes it possible to use only one or two multispectral cameras for each conveying line.

It goes without saying that the invention can be the object of numerous variations other than the embodiments described above and illustrated in the figures.

The invention claimed is:

1. Method of optically analysing objects belonging to the fruit and vegetable group in which images representative of the objects are produced in different imaging wavelength ranges,
wherein:
  a plurality of light sources formed of light-emitting diodes (LED1, LED2, LED3, LED4, LED5) are arranged to be able each to apply light radiation to at least an external surface portion of at least one object, named illuminated object (6), the different light sources being adapted to be able to apply light radiation in different illumination wavelength ranges selectively to each illuminated object,
  the light radiation from at least one light source is applied to the whole of a visible face of the external surface of each object illuminated by this light source,
  the light sources are controlled according to a predetermined illumination sequence for each illuminated object in succession according to said different illumination wavelength ranges,
  images are produced by at least one colour camera (4, 4$a$, 4$b$) sensitive to light radiation in the visible range and to light radiation in the infrared range, named multispectral camera (4, 4$a$, 4$b$), said at least one multispectral camera being orientated towards an external surface portion of at least one illuminated object corresponding to the whole visible face of the external surface of the object on the optical axis of the multispectral camera, and the exposure of said at least one multispectral camera being controlled in synchronism with said illumination sequence so as to produce, with this same multispectral camera, a plurality of images in different imaging wavelength ranges of said external surface portion of at least one illuminated object (6), said plurality of images including at least one image in a visible range and at least one image in an infrared range, each multispectral camera (4, 4a, 4b) is chosen from the group of cameras comprising a CMOS sensor with a matrix of colour filters without an infrared cut-off filter; and cameras comprising three CMOS sensors, one CMOS sensor for each primary colour, without an infrared cut-off filter.

2. Method according to claim 1, wherein said plurality of images of said external surface portion produced by a single multispectral camera (4, 4a, 4b) is recorded in a buffer memory (42a, 42b) of this multispectral camera.

3. Method according to claim 2, wherein each image in an infrared range is produced with an adjustment of the white balance according to the sensitivity for each colour of said at least one multispectral camera (4, 4a, 4b) in said infrared range.

4. Method according to claim 2, wherein said illumination sequence is formed of a succession of illumination periods, some of said light sources (LED1, LED2, LED3, LED4, LED5) being activated during each illumination period, this group of said light sources being chosen to illuminate each object in one of said illumination wavelength ranges, wherein each illumination period is between 0.1 ms and 5 ms, and wherein the exposure of said at least one multispectral camera (4, 4a, 4b) is trigged with a delay with respect to the activation of an illumination period, this delay being chosen so that each light source of said group of said light sources (LED1, LED2, LED3, LED4, LED5) of this illumination period is effectively completely switched on and active before said at least one multispectral camera is triggered.

5. Method according to claim 2, wherein said plurality of images produced by a single multispectral camera comprises:
an image produced by reflection while the object is illuminated by white light,
an image produced by reflection while the object is illuminated in an infrared illumination range at a wavelength between 720 and 780 nm,
an image produced by reflection while the object is illuminated in an infrared illumination range at a wavelength between 800 nm and 850 nm,
an image produced by reflection while the object is illuminated in an infrared illumination range at a wavelength between 900 nm and 1000 nm,
an image produced by reflection while the object is illuminated in an ultraviolet illumination range at a wavelength between 250 nm and 380 nm.

6. Method according to claim 1, wherein each image in an infrared range is produced with an adjustment of the white balance according to the sensitivity for each colour of said at least one multispectral camera (4, 4a, 4b) in said infrared range.

7. Method according to claim 6, wherein said illumination sequence is formed of a succession of illumination periods, some of said light sources (LED1, LED2, LED3, LED4, LED5) being activated during each illumination period, this group of said light sources being chosen to illuminate each object in one of said illumination wavelength ranges, wherein each illumination period is between 0.1 ms and 5 ms, and wherein the exposure of said at least one multispectral camera (4, 4a, 4b) is trigged with a delay with respect to the activation of an illumination period, this delay being chosen so that each light source of said group of said light sources (LED1, LED2, LED3, LED4, LED5) of this illumination period is effectively completely switched on and active before said at least one multispectral camera is triggered.

8. Method according to claim 6, wherein said plurality of images produced by a single multispectral camera comprises:
an image produced by reflection while the object is illuminated by white light,
an image produced by reflection while the object is illuminated in an infrared illumination range at a wavelength between 720 and 780 nm,
an image produced by reflection while the object is illuminated in an infrared illumination range at a wavelength between 800 nm and 850 nm,
an image produced by reflection while the object is illuminated in an infrared illumination range at a wavelength between 900 nm and 1000 nm,
an image produced by reflection while the object is illuminated in an ultraviolet illumination range at a wavelength between 250 nm and 380 nm.

9. Method according to claim 1, wherein said illumination sequence is formed of a succession of illumination periods, some of said light sources (LED1, LED2, LED3, LED4, LED5) being activated during each illumination period, this group of said light sources being chosen to illuminate each object in one of said illumination wavelength ranges, wherein each illumination period is between 0.1 ms and 5 ms, and wherein the exposure of said at least one multispectral camera (4, 4a, 4b) is trigged with a delay with respect to the activation of an illumination period, this delay being chosen so that each light source of said group of said light sources (LED1, LED2, LED3, LED4, LED5) of this illumination period is effectively completely switched on and active before said at least one multispectral camera is triggered.

10. Method according to claim 9, wherein for the production of reflection images the external surface region of the object illuminated by at least one light source is the whole of a face of the external surface of the object visible by the light radiation of this light source, and wherein at least one multispectral camera is arranged with respect to this light source to produce reflection images of the whole of this visible face.

11. Method according to claim 1, wherein said plurality of images produced by a single multispectral camera comprises:
an image produced by reflection while the object is illuminated by white light,
an image produced by reflection while the object is illuminated in an infrared illumination range at a wavelength between 720 and 780 nm,
an image produced by reflection while the object is illuminated in an infrared illumination range at a wavelength between 800 nm and 850 nm,
an image produced by reflection while the object is illuminated in an infrared illumination range at a wavelength between 900 nm and 1000 nm,
an image produced by reflection while the object is illuminated in an ultraviolet illumination range at a wavelength between 250 nm and 380 nm.

12. Method according to claim 1, wherein each illuminated object (6) is rotated on itself and is moved by a conveyor during said illumination sequence.

13. Device for optically analysing objects belonging to the fruit and vegetable group, comprising means for producing images of the objects in different wavelength ranges, further comprising:
- an illumination device comprising a plurality of light sources formed of light-emitting diodes (LED1, LED2, LED3, LED4, LED5) arranged to be able each to apply light radiation to at least an external surface portion of at least one object, named illuminated object, the different light sources being adapted to be able to apply light radiation in different illumination wavelength ranges selectively to each illuminated object,
- the illumination device being adapted to be able to apply light radiation from at least one light source to the whole of a visible face of the external surface of each object illuminated by this light source,
- a control device (10, 20, 43a, 43b) adapted to be able to control these light sources according to a predetermined sequence of illumination of each illuminated object in succession according to the different illumination wavelength ranges,
- at least one colour camera sensitive to light radiation in the visible range and to light radiation in the infrared range, named multispectral camera (4, 4a, 4b), orientated towards an external surface portion of at least one illuminated object corresponding to the whole visible face of the external surface of the object on the optical axis of the multispectral camera,
- each multispectral camera (4, 4a, 4b) being chosen from the group of cameras comprising a CMOS sensor with a matrix of colour filters without an infrared cut-off filter; and cameras comprising three CMOS sensors, one CMOS sensor for each primary colour, without an infrared cut-off filter, and wherein said control device (10, 20, 43a, 43b) is adapted to control the exposure of each multispectral camera (4, 4a, 4b) in synchronism with said illumination sequence so as to produce, with this same multispectral camera, a plurality of images in different imaging wavelength ranges of said external surface portion of at least one illuminated object, said plurality of images including at least one image in a visible range and at least one image in an infrared range.

14. Device according to claim 13, wherein said light sources are mounted in an optical chamber (2) having a reflective internal surface of a shape which is chosen depending on the position of the light sources so as to permit uniform illumination of the objects in the optical field of said at least one multispectral camera.

15. Device according to claim 13, wherein, for the production of each image in an infrared range, said control device (10, 20) is adapted to adjust the white balance according to the sensitivity of each colour of said at least one multispectral camera in said infrared range.

16. Device according to claim 13, wherein each multispectral camera (4, 4a, 4b) is a colour camera comprising a CMOS sensor and a colour filter matrix, without an infrared cut-off filter, and fitted with a buffer memory (42a, 42b) for storing the images.

17. Device according to claim 13, wherein said light sources (LED1, LED2, LED3, LED4, LED5) comprise a least one visible white light illumination LED, at least one ultraviolet light radiation illumination LED and at least one infrared illumination LED.

18. Device for automatically sorting objects belonging to the fruit and vegetable group according to predetermined sorting criteria comprising:
- at least one conveying line (8) able to transport the objects in front of stations for analysing the objects in accordance with said sorting criteria, including at least one optical analysis station,
- an automated machine (10) connected to the analysis stations to receive analysis signals therefrom,
- stations for discharging the objects in a plurality of discharging regions, the automated machine being programmed to control the selective discharging of each object in a discharging region selected in accordance with the analysis signals received by this automated machine for this object, further comprising at least one optical analysis station formed by an optical analysis device (3) according to claim 13.

19. Device according to claim 18, wherein each optical analysis station comprises less than four multispectral cameras (4a, 4b) per conveying line.

20. Device according to claim 18, further comprising a single optical analysis station (3).

* * * * *